United States Patent [19]

Herrmann et al.

[11] Patent Number: 5,202,233
[45] Date of Patent: Apr. 13, 1993

[54] PROCESS FOR THE DETECTION OF SUBSTANCES WITH HYDROLASE ACTIVITY

[75] Inventors: Rupert Herrmann; Hans-Joachim Guder, both of Weilheim; Werner Güthlein; Manfred Kuhr, both of Mannheim, all of Fed. Rep. of Germany; Johann Berger; Harvey Buck, both of Indianapolis, Ind.

[73] Assignee: Boehringer Mannheim GMBH, Mannheim, Fed. Rep. of Germany

[21] Appl. No.: 816,795

[22] Filed: Jan. 3, 1992

Related U.S. Application Data

[63] Continuation of Ser. No. 217,383, Jul. 11, 1988, abandoned.

[51] Int. Cl.$^5$ .......................................... G01N 33/573
[52] U.S. Cl. ......................................... 435/7.4; 435/805
[58] Field of Search ................... 436/518, 545; 435/18, 435/180, 805, 19, 21, 23, 7.4

[56] References Cited

U.S. PATENT DOCUMENTS

| | | | |
|---|---|---|---|
| 4,391,904 | 7/1983 | Litman et al. | 435/810 |
| 4,738,920 | 4/1988 | Ishiguro | 435/7.4 |

FOREIGN PATENT DOCUMENTS

| | | |
|---|---|---|
| 0025227 | 3/1981 | European Pat. Off. |
| 87/01698 | 3/1987 | European Pat. Off. |

OTHER PUBLICATIONS

Gossrau *Histochemie* 35:199; 1973.
Gossrau, R. (I) *Histochemie* 37:89–91, 1973.
Gossrau (II) *Hisochem. J.* 8:271–282, 1976.
Gossrau (III) *Histochemie* 35:199–218, 1973.
Marvin Nachlas et al., Evidence for specificity of Eseuse & Lipase by use of 3 chromogenic substances, J. of Biol. Chem. vol 181, 1944 pp. 343–355.

A. Vallec et al., Enzyme Immunoassays, pp. 77–86, Alternative Immunoassays Ed. W. P. Collins, 1985.
(List continued on next page.)

*Primary Examiner*—Mary E. Ceperley
*Attorney, Agent, or Firm*—Felfe & Lynch

[57] ABSTRACT

A process for the detection of substances with hydrolase activity in a sample by mixing the sample with a hydrolase substrate and an oxidizing agent, and the evaluating the resultant color intensity, wherein, as hydrolase substrate, there is used at least one compound of the formula

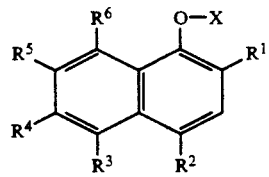

in which
$R^1$ is hydrogen or an alkoxy radical,
$R^2$ is hydrogen or halogen, an amino group or an alkoxy or aralkoxy radical,
$R^3$, $R^4$, $R^5$ and $R^6$, which can be the same or different, are hydrogen, halogen, carboxyl, a carbamoyl group, sulpho, an amino groups alkyl, an alkoxy radical, aralkoxy, alkylcarbonyl or alkoxycarbonyl, and
X is a glycosyl, phosphate or acyl residue.

Optionally $R^2$ and $R^3$, $R^3$ and $R^4$, $R^4$ and $R^5$, and $R^5$ and $R^6$ can be joined to form a ring system. At least one of $R^1$ and $R^2$ must be hydrogen and at least one of $R^1$, $R^2$ and $R^3$ must not be hydrogen. Compounds in which X is β-galactosyl are new.

9 Claims, 1 Drawing Sheet

OTHER PUBLICATIONS

Romeo Wagner, et al., Synthetic Organic Chemistry John Wiley & Sons Inc. 1953, pp. 226–229, and 480–483.

George G. Guilbault, et al., 4-Methoxy-α-Naphthal as a spectrophotometric Dgt. Substance for Peroxidase, pp. 2494–2496, Anal. Chem. vol. 36 No. 13, Dec. 1964.

Richard Cohen, et al., Colorimatic Estimation & Hist. Chem. Dem. of B-D-gal. J. of Biol. Chem. vol. 195, 1952 pp. 239–249.

Herbert Ravin, et al., Colorimetric Estimation of Carboxy peptidase activity J. of Biol. Chem. vol. 190, 1951, pp. 391–402.

Arnold Seligman, Colorimation Determination of Phosphatases in Human Serum J. of Biol. Chem. vol. 190, 1951, pp. 7–15.

E. Strauss & R. Gossrau, "Die Hydrolasen des Dünndarmepithels beim Meerschwrinen . . . ", *Z. Mikros-Anat. AS*, 721 (1981).

T. Lud-Hansen et al., "A Quantitative Cytochemical Assay of B-Calactosidese in Sinle . . . ", *Histochem.* 81, 321 (1984).

PROCESS FOR THE DETECTION OF SUBSTANCES WITH HYDROLASE ACTIVITY

This is a continuation of application Ser. No. 217,383 filed on Jul. 11, 1988, now abandoned.

BACKGROUND OF THE INVENTION

The present invention is concerned with a process for the detection of substances with hydrolase activity and with an agent suitable for carrying out the process, as well as with new hydrolase substrates and processes for the preparation thereof.

Hydrolases are enzymes which have recently achieved great importance. On the one hand, they play an important role in the metabolism of plants and animals and also of humans. If the concentration of a hydrolase in one of these biological systems deviates from the concentration normally present therein, then this can be the cause of a disease. Therefore, it is a task of clinical diagnosis, in the case of the presence of a disease, to ascertain, by determination of the concentration of a hydrolase in body fluids, possible deviations from the normal value. This preferably takes place via the determination of the hydrolase activity by means of an indicator reaction. For this purpose, the sample to be investigated is mixed with a substrate for the hydrolase in question. The amount of product formed from the substrate is a measure for the hydrolase concentration present.

On the other hand, hydrolases are used ever more frequently as enzymes for labelling immunologically active compounds. $\beta$-Galactosidase is hereby especially widely used for the labelling of, for example, antibodies in immunological tests (see Annals of Clinical Biochemistry, 16, 221/1979). Tests of this kind serve to determine the content of an immunologically active analyte in a sample. They are so constructed that the concentration of the analyte is determined via an appropriate immune component which carries covalently bound $\beta$-galactosidase as label. The test is so constructed that the concentration of the immune partner is directly dependent upon the concentration of the analyte to be determined. The concentration of the labelled immune component is also made visible via an indicator reaction, in which the immune component labelled with $\beta$-galactosidase-is reacted with a substrate for $\beta$-galactosidase.

The amount of product formed is proportional to the concentration of the immune component. By comparison with the values of a calibration curve, which is produced with the help of samples with known analyte concentration, an unknown analyte concentration in a sample can be determined.

Hydrolases are also used as enzymes for labelling nucleic acids in processes for the detection of nucleic acids. Such a process which uses $\beta$-galactosidase as enzyme label is described in Federal Republic of Germany Patent Specification No. 29 15 082. Here, too, the amount of label is determined in an indicator reaction.

Furthermore, hydrolases are used as reagents in research. Here, too, it is important to be able to determine the concentration of the enzymes exactly and quickly. In general, for this purpose, there are used methods which are similar to those used in clinical diagnosis.

The substrate used is generally a chemical compound which is soluble in the sample liquid. In the case of the reaction with the hydrolase, a product is formed which differs in one of its characteristics, for example a characteristic light absorption, a light emission (fluorescence) or the like, from the substrate and can thereby be determined.

In the case of test processes on immunologically active substances, a differentiation is made between two technical embodiments. In the case of a frequently used embodiment, the detection reaction takes place in a cuvette such as is generally used for photometric investigations. The evaluation of the indicator reaction is then carried out by measurement of the absorption, emission or radio-activity in an appropriate apparatus.

In the case of another embodiment, the reactions take place in one or more fleece or films which are parts of a test carrier, the necessary reagents being applied to these fleece or films. The amount of product which is liberated by the hydrolase activity from the hydrolase substrate during the indicator reaction can then be determined directly in such a fleece or film. An advantage of this embodiment is that it is possible to work with only a single solution, the liquid sample, which considerably simplifies the carrying out of the process. The amount of product formed can be detected especially simply by measurement of the light absorption at a particular wavelength.

Substrates suitable for this purpose include the phenyl-sulphophthaleinyl-$\beta$-D-galactosides and derivatives thereof, which are described in European Patent Specification No. 01 46 866, from which phenolsulphophthalein derivatives are liberated by reaction with $\beta$-D-galactosidase. Whereas the substrate has a yellow colour, the product is red coloured. Thus, during the indicator reaction, a gradual colour change from yellow via orange to red takes place. The colour change can only be assessed very inaccurately with the naked eye so that an appropriate photometer must be used for the measurement.

The resorufin-$\beta$-D-glycosides described in European Patent Specification No. 0 156 347 are also substrates in which case the reaction with a glycosidase causes a colour change from yellow to red to take place. It has been ascertained that in the transitional region between yellow and red, especially in the case of low $\beta$-glycosidase activities, the visual evaluation leads to subjective results, for which reason apparatus are here also used for the evaluation. However, these apparatus are relatively complicated and, therefore, expensive. The resorufin glycosides are not very suitable, as substrates for use in test carriers since resorufin formed from them bleeds out.

Hydrolase substrates such as, for example methylumbelliferone galactoside, in which hydrolysis causes only a change of the fluoresence properties, are also unsuitable for a visual evaluation. Methylumbelliferone galactoside also gives rise to a substance which easily bleeds out of the test strips.

Furthermore, processes for the detection of substances with hydrolase activity have been suggested in which uncoloured hydrolase substrates are used which, in the case of reaction with a hydrolase, are converted into coloured products. Consequently, in the case of these detection reactions, the formation of a colour is to be assessed rather than a colour change. This can take place in a simple way by comparison of the colour intensity with a colour shade of a colour scale. Even colour-blind persons can evaluate such a test.

5-Bromo-4-chloro-3-indolyl-$\beta$-galactoside is such a substrate. This substrate forms after cleavage and oxidation a product which does not bleed out strongly from test carriers. However, the substrate itself has a low water-solubility and is cleaved only slowly by β-galactosidase. Therefore, the resultant colour formation is not very intensive. A test constructed thereon is thus not suitable for a rapid visual evaluation.

In Biochem. Z., 333, 209/1960, compounds are suggested as substrates, the hydrolysis of which liberates phenols. However, these readily bleed out of test carriers. In the case of nitrophenol, a more or less intensive yellow coloration develops during the indicator reaction. In the case of this wavelength, the visual evaluation in the range of small concentrations is also very unfavourable.

For improving visibility, in an additional reaction the liberated phenols are oxidatively coupled with aminoantipyrine or methylbenzothiazolinone hydrazone (Anal. Biochem., 40, 281/1971) or with diazonium salts to give coloured azo materials (see, for example, Histochemie, 37, 89/1973). Some of these coloured materials are admittedly suitable for use in test carriers since they do not bleed out so easily, but the use of this coupling reaction is disadvantageous for other reasons. Thus, for the carrying out of the test on a fleece or film, all the reagents necessary for this additional reaction must also be applied to a fleece or incorporated into a film. The large number of reagents, for example coupling components, complicates the carrying out of the test and gives rise to numerous disadvantages and difficulties. Thus, in individual cases, care must be taken that the reagents not react prematurely with one another or non-specifically with other components of the sample solution. Thus, aminoantipyrine or methylbenzothiazolinone hydrazone also react with components present, for example, in a urine sample to be investigated and thus falsify the measurement. Other coupling components, such as diazonium salts, impair the storage stability. In the case of the choice of the reagents, it is also to be taken into account that they do not themselves already possess an inherent colour.

Bleeding out phenomena, which occur on test carriers in the case of some of the dyes formed, give, for example, the result that the colour intensity is not the same at all places on the fleece or film. This gives rise to disadvantages in the evaluation since, for example, the measurement values are falsified.

Therefore, there is a need for a process in which the described disadvantages are avoided and with the help of which substances with hydrolase activity can also be detected on test carriers in a simpler, quicker and more dependable way.

It is an object of the present invention to satisfy this need.

SUMMARY OF THE INVENTION

Thus, according to the present invention, there is provided a process for the detection of substances with hydrolase activity in a sample by mixing the sample with a hydrolase substrate, as well as with an oxidation agent, and evaluating the resultant colour intensity, wherein, as hydrolase substrate, there is used at least one compound of the general formula:

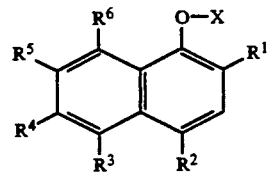

(I)

in which $R^1$ is a hydrogen atom or an alkoxy radical, $R^2$ is a hydrogen or halogen atom, an alkoxy or aralkoxy radical or an amino group, $R^3$, $R^4$, $R^5$ and $R^6$, which can be the same or different, are hydrogen or halogen atoms, alkyl, alkoxy, aralkoxy, alkoxycarbonyl or alkylcarbonyl radicals or carboxyl, carbamoyl, sulpho or amino groups and X is a glycosyl, phosphate or acyl radical, in which the radicals $R^2$ and $R^3$, $R^3$ and $R^4$, $R^4$ and $R^5$, as well as $R^5$ and $R^6$, can, in each case, be joined to form a ring system, at least one of the symbols $R^1$ and $R^2$ signifies a hydrogen atom and at least one of the symbols $R^1$, $R^2$ and $R^3$ does not signify a hydrogen atom.

DETAILED DISCLOSURE

Figure 1:
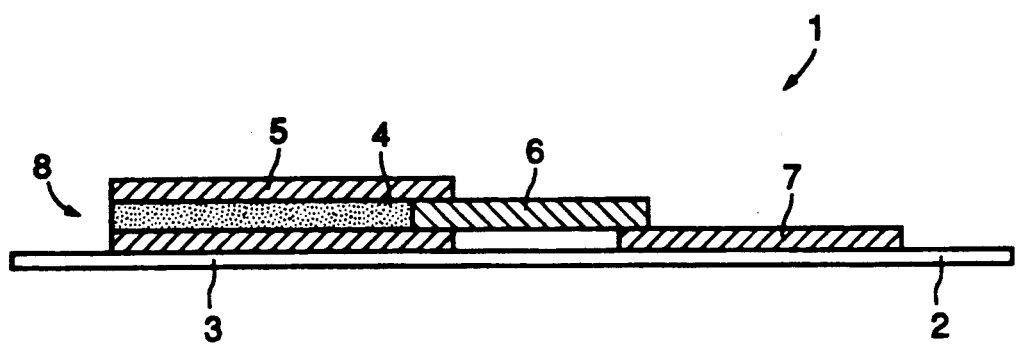
FIGS. 1 and 2 illustrate test strips which are usuable in practising the process of this invention. They are more fully described in Examples 10 and 11.

The alkoxy radicals $R^1$, $R^2$, $R^3$, $R^4$, $R^5$ and $R^6$ preferably contain up to 4 carbon atoms which can form a chain or are branched, the methoxy, isopropoxy, n-propoxy and n-butoxy radicals being especially preferred.

The alkoxy radicals $R^1$, $R^2$, $R^3$, $R^4$, $R^5$ and $R^6$ can be unsubstituted or substituted one or more times. Preferred substituents include halogen atoms and amino groups. Preferred substituted radicals are the 1,1,1-trifluoroeth-2-oxy and 1-bromoeth-2-oxy radicals. The alkoxy radical can also signify the radical —O—(CH$_2$—CH$_2$O)$_n$—R$^7$, wherein n is a whole number of from 1 to 3 and $R^7$ is a hydrogen atom or an alkyl radical containing up to 4 carbon atoms and preferably a methyl radical or signifies a compound of general formula (I).

The alkyl radicals $R^3$, $R^4$, $R^5$ and $R^6$ are preferably hydrocarbon radicals containing up to 4 carbon atoms, the methyl radical being especially preferred.

The aralkoxy radicals $R^2$, $R^3$, $R^4$, $R^5$ and $R^6$ preferably contain up to 4 carbon atoms in the alkyl moiety and 6 to 10 carbon atoms in the aryl moiety, the benzyloxy radical being especially preferred.

As halogen in the definitions of the symbols $R^2$, $R^3$, $R^4$, $R^5$ and $R^6$, there is to be understood fluorine, chlorine, bromine or iodine, chlorine being preferred.

The alkyl moieties of the alkylcarbonyl radicals preferably contain up to 4 carbon atoms and the alkoxy moieties of the alkoxycarbonyl radicals preferably also contain up to 4 carbon atoms.

The amino groups $R^2$, $R^3$, $R^4$, $R^5$ and $R^6$, as well as the carbamoyl groups, can be unsubstituted or substituted once or twice. Preferred substituents include acyl radicals and unsubstituted and substituted alkyl radicals, the acetyl radical being especially preferred as the acyl radical.

Glycosyl radicals X are mono-, oligo- and polysaccharide radicals of the hexosepyranoside series, the monosaccharide radicals being preferred. The hexosepyranosides are preferably the glucoside and galactoside radicals. Of these, in turn, the β-glycosides have proved to be especially preferable.

Acyl radicals X preferably contain up to 20 carbon atoms and can be saturated or unsaturated, straight-chained or branched, the acetyl radical being especially preferred. The acyl radicals also include aminoacyl radicals, preferred aminoacyl radicals being the residues of the naturally-occurring α-L-amino acids bound via the carbonyl function. The free polar residues of the amino acids, for example the amino function, can thereby be protected by appropriate protective groups. An especially preferred amino acid residue is the alanyl residue which carries a tosyl radical on the amino function.

The phosphate radical is the —$PO_3H_2$ radical and the salts thereof. All positively charged ions can serve as cations in these salts. The alkali metal, alkaline earth metal and ammonium ions are preferred, sodium, potassium, magnesium and calcium ions being especially preferred.

When $R^2$ and $R^3$ are joined to form a ring system, compounds are preferred in which oxygen atoms or amino groups of the radicals $R^2$ and $R^3$ are so bound that a 6-membered ring is obtained. Preferred rings which have been so formed include especially the 2,2-dimethyl-1,3-dioxine and the 2,2-dimethyl-3-oxazine rings.

When $R^3$ and $R^4$ or $R^5$ and $R^6$ are joined to form a ring, an aromatic system is preferred as the ring system, benzanellated compounds being especially preferred.

When $R^4$ and $R^5$ are joined to form a ring system, ring systems with 5 or 6 carbon atoms are preferred.

The compounds of general formula (I) can be prepared by the reaction of compounds of the general formula:

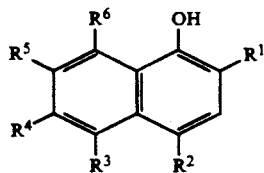

(II)

in which $R^1$ to $R^6$ have the above-given meanings, with compounds of the general formula:

 X—Y (III)

in which X has the above-given meaning and Y is a reactive group.

When X is a glycosyl radical, a process must be used which avoids an oxidation of the highly oxidation-sensitive aglycone component II during the reaction. Classical processes, such as the Koenigs-Knorr reaction and analogous processes derived therefrom, which use silver salts or oxidatively-acting heavy metal salts, cannot be used in the present case since the naphthol derivatives employed would be immediately oxidised to the coloured material.

The naphthols of general formula (II) are reacted with an activated sugar of general formula (III) in aqueous alkali metal hydroxide solution. Compounds in which Y is a nucleophilic group which is removed especially well, for example halogen, especially fluorine, chlorine or bromine, or a sulphonyloxy radical, especially a toluenesulphonyloxy or methanesulphonyloxy radical, have proved to be especially suitable. It has thereby proved to be desirable to keep the free hydroxyl groups of the sugar or amino groups on the naphthyl radical protected by appropriate protecting groups during the reaction.

When X is an acyl radical, processes can be used such as are known for the preparation of esters from alcohols as well as special phenols by reaction with organic carboxylic acids. Before esterification, functional groups of the amino acids are preferably masked by appropriate protecting groups. After the reaction, the protecting groups can be split off again. The reactive group Y is preferably a nucleophilic group which is removed especially well, halogen, alcoholate and carboxylate being hereby especially advantageous. Such a preparation is, for example, described in Liebigs Ann. Chem., 1984, 319-339 and in European Patent Specification No. 0,039,880.

For the preparation of compounds of general formula (I), in which X is a phosphate residue, compounds of general formula (III) are especially preferred in which X is a —$POZ_2$ or —$PZ_4$ radical in which Z is a readily removable group, especially an alcoholate containing up to 4 carbon atoms or chloride, bromide or iodide, and Y is a halide residue, preferably chloride, bromide or iodide, or an alcoholate. Phosphorus oxychloride is especially preferred as a compound of general formula X—Y. It is preferable to mask free amino groups of the compound of general formula (II) by protective groups which can be split off after the reaction.

Compounds in which X is a —$POZ_2$ or —$PZ_4$ group can be converted into the phosphates by hydrolysis in known manner.

The salts of the phosphates can be prepared from the acids in known manner, for example by ion exchange.

The compounds of general formulae (II) and (III) are known compounds or can be prepared analogously to known processes of organic synthesis (see Liebigs Ann. Chem., 319/1984; 2420/1985; 1847/1985; 251/1985; 140/1980; 297/1987; 1321/1980; Z. Naturforsch., 40b, 534/1985; 41b, 377/1986). In particular, 4-methoxy-1-naphthol is known from J. prakt. Chem., 62, 30/1900 which can be reacted oxidatively to a blue coloured material (the so-called Russig's indigo). This oxidation was used in Analytical Chemistry, 36, 2494/1964 for the detection of peroxidases.

Thus, although some 4-methoxy-1-naphthol derivatives, as well as the possibility of converting 4-methoxy-1-naphthol oxidatively into a coloured material, have been known for many years, hitherto methoxynaphthol derivatives have not been used as hydrolase substrates in processes for the detection of compounds with hydrolase activity in which, without the addition of a further coupling element, the formation of a coloured material is brought about oxidatively.

Surprisingly, the new compounds of general formula (I) according to the present invention are outstandingly suitable as hydrolase substrates. They are water-soluble, colourless and stable so long as they do not come into contact with a hydrolase. If an extraordinarily good water solubility is desired, then it is preferred to use compounds of general formula (I) in which one or more of the residues $R^3$, $R^4$, $R^5$ and $R^6$ is a polar group, for example a carboxyl or sulpho group.

Compounds in which the water-solubility of the substrate is greatly reduced by an accumulation of lipophilic residues can also be used as hydrolase substrates if one is willing to tolerate the disadvantage of lowering the polarity of the solvent in which the reaction takes place by adding, for example, an appropriate organic solvent or detergent, which again increases the solubility.

A compound is described as a hydrolase substrate if on reaction of the substance in question with hydrolase activity, two products are formed from said substrate, with the take up of water. The reaction thereby follows the laws known in enzyme kinetics. It is a prerequisite that the substrates are soluble at least to the greater part in the solution containing the substance with hydrolase activity.

As hydrolase substrates in the process according to the present invention, there are especially preferred those compounds of general formula (I) in which the molecule component X is analogous to a molecule component of the natural substrate of the corresponding hydrolase. Thus, for example, as β-galactosidase substrates, there are especially preferred compounds of general formula (I) in which X is a β-galactoside residue, as esterase substrates those in which X is an acyl radical and as phosphatase substrates compounds of general formula (I) in which X is a phosphate residue.

Substances with hydrolase activity are those which can cleave chemical compounds into two products with the consumption of water. To these belong naturally occurring and artificially produced hydrolases of the enzyme main class 3. The process according to the present invention has proved to be especially useful for the detection of glycosidases, preferably of galactosidase, and of esterases, preferably of lipases and phosphatases.

By substances with hydrolase activity are also to be understood compounds of these hydrolases with other chemical compounds, for example immunologically active compounds or nucleic acids. To the immunologically active compounds belong, for example, haptens, antigens, antibodies and immune complexes but also fragments of antibodies, such as the Fab and F(ab')$_2$ fragments. The compounds of the hydrolases with these immunologically active compounds are referred to as hydrolase conjugates, the hydrolase thereby serving for the labelling of the immunologically active compound. The process according to the present invention is especially suitable for the detection of immunologically active compounds with alkaline or acid phosphatase or β-galactosidase as label.

By a sample there is thereby preferably to be understood a solid or liquid sample.

In the case of a solid sample, a distinction can be made between soluble and substantially insoluble samples.

A soluble sample is preferably converted into a liquid sample for the detection according to this invention.

By a substantially insoluble sample there is preferably to be understood a solid material on the outer or inner surface of which is bound a substance with hydrolase activity. The nature of the binding is not of importance for the process according to the present invention. This binding can be, for example, not only covalent but also ionic or adsorptive or also biospecific. Biospecific bonds are bonds between biological binding components, for example the bonds between substances acting as antigen or hapten and antibodies, biotin and avidine or streptavidine and complementary nucleic acids.

By a liquid sample in which the substances with hydrolase activity are to be detected are to be understood essentially aqueous solutions. These solutions can be, for example, solutions of a hydrolase or hydrolase conjugate in water. Admixtures, such as salts, detergents and the like, are often added to these solutions, for example for increasing the storage stability. The process according to the present invention can also be employed in such solutions. The liquid sample can also be a body fluid or a liquid obtained therefrom by the addition or separation of components. These include, for example, blood, blood plasma, serum and urine.

The liquid sample can preferably also be a liquid such as results in the course of an immunological test process. These are, for example, those described in Annals of Clinical Biochemistry, 16, 221/1979, and their advantageous further developments which are known to the expert in the field of immunoassays. Substances with hydrolase activity can also be detected in such liquids with the process according to the present invention. These solutions usually contain buffer substances, stabilisers, wetting agents and the like which, however, do not decisively disturb the detection.

The concentration of substances with hydrolase activity can be determined advantageously in a range of from $10^{-6}$ to $10^{-15}$ mole/liter and especially of from $10^{-6}$ to $10^{-12}$ mole/liter.

The process can be used for sample solutions in which the pH value is from 5 to 11 and preferably from 6 to 10. The optimum pH value at which the process is carried out depends upon the hydrolase used. For the rapid carrying out of the process, it is preferable to work at or in the neighbourhood of the pH value at which the hydrolase displays an activity maximum. Outside of this range, there can take place a noticeable, non-enzymatic hydrolysis or inactivation of the hydrolase The detection reaction is preferably carried out in an absorbent or swellable carrier. Such carriers are, for example, fleece or films, fleece being preferred. By fleece are to be understood paper-like materials made up of fibres. As fibre materials, there are preferably used cellulose, synthetic resins or mixtures thereof. Sponge-like and/or porous carriers can also be used.

However, the reaction can also be carried out in a vessel of any desired shape, for example in a cuvette. If the course of the reaction is to be monitored by means of an absorption photometer, those compounds of general formula (I) are especially preferred in which products are formed which are soluble in the reaction medium. One possibility is the use of compounds of general formula (I) in which, depending upon the polarity of the reaction medium, one or more of the residues $R^3$, $R^4$, $R^5$ and $R^6$ is a polar group, for example a carboxyl or sulpho group. A further possibility for the detection of substances with hydrolase activity in solution is the addition of solvents lowering the polarity of the reaction medium, for example organic solvents or detergents. Insofar as the disadvantage of these additional components is taken into account, the solubility of the hydrolysis products is increased.

For the development of a colour during the indicator reaction, the presence of an oxidation agent is necessary. As oxidation agents, there can be used those substances or mixtures of substances the oxidation potential of which lies above the value for the free naphthol, potassium ferricyanide, perborate/peroxidase, peroxide/peroxidase, tetrazolium salts and oxygen/bilirubin oxidase having proved to be especially advantageous.

For carrying out the process according to the present invention, the sample is mixed with the appropriate hydrolase substrate and an oxidation agent.

The mixing of the sample with the hydrolase substrate can take place in various ways.

The mixing of the sample with the hydrolase substrate and the oxidation agent can take place simultaneously or successively.

In the case of a liquid sample, for example of a solution of the substance with hydrolase activity, the hydrolase substrate or the oxidation agent can be added, for example, in the form of a solid material, for example of a powder, tablet, lyophilisate or the like, or in the form of a solution to the sample.

If the detection reaction takes place in an absorbent or swellable carrier, then it has proved to be especially preferable to apply the sample to a carrier on which is impregnated the hydrolase substrate, as well as possibly the oxidation agent and additional materials. For the impregnation, there is prepared a solution of the said materials and the carrier material is impregnated therewith, the impregnated carrier material subsequently being dried.

When the carrier is a film, the hydrolase substrate, as well as possibly the oxidation agent and additional materials, are already incorporated during the production of the film.

If the oxidation agent is not present together with the hydrolase substrate, the oxidation agent is mixed with the sample before or after mixing the sample with the hydrolase substrate.

If the detection reaction takes place in a vessel, then it has proved to be especially preferable to use the hydrolase substrate in solid form or as a solution, possibly mixed with the oxidation agent and with additional materials. Here, too, the oxidation agent or the additional materials can be added separately.

In the case of a solid sample, for example when the substance with hydrolase activity is bound to a carrier material, it is preferred to add the hydrolase substrate and/or the oxidation agent to the sample in the form of a solution. However, it is, for example, also possible first to mix the components and then to add a liquid for the preparation of a solution.

It is important for the success of the detection reaction that the hydrolase substrate can so enter into contact with the substance with hydrolase activity present in the sample that the enzyme reaction can take place.

During the indicator reaction, a strong colour is formed which, depending upon the nature of the substitution, extends from red via blue to turquoise. The colour intensity can be measured according to known processes with photometers but especially with reflection photometers. For this purpose, light is beamed in of a wavelength which the product of the indicator reaction can absorb. Preferred is a wavelength of from 550 to 750 nm and especially of from 600 to 700 nm.

The colour intensity is compared with the values of a calibration curve which is obtained by measurement of the values for samples with known concentrations of substances with hydrolase activity, each intensity being associated with a particular concentration. This comparison is preferably carried out with the help of a calculator.

Insofar as a colour change does not have to be observed but rather a colour development, the evaluation with the human eye is also possible, this having the advantage that an apparatus does not have to be used. Possible sources of error thus disappear, such as a incorrect use of the apparatus and the like.

The process according to the present invention can be used for the qualitative as well as for the quantitative detection of substances with hydrolase activity. For the qualitative evaluation, it is observed whether a coloration has taken place. For the quantitative determination, at a fixed point of time the colour is compared visually with a colour scale which associates each colour with a definite concentration.

The process according to the present invention can be used with especial advantages particularly on test carriers. The advantages are, for example, that the process is simple and inexpensive but, nevertheless, gives dependable results. The process is, for example, simple in that it can also be evaluated visually so that expensive apparatus are thereby not necessary. It is especially dependable since it does not lead to bleeding out phenomena on the test carriers, this being of great advantage.

By test carriers are to be understood agents for the detection of substances by carrying out a test. They usually comprise a base plate or film on to which are applied the reagents necessary for the test, usually by means of fleece or films.

In the process according to the present invention, no further coupling components, for example diazonium salts, are used since these lead to side reactions or losses of stability.

In the case of immunological test processes, samples are also obtained which are to be investigated for their content of substances with hydrolase activity and especially of hydrolase conjugates.

The process according to the present invention for the detection of a substance with hydrolase activity thus can find special use, for example, in immunological processes for the detection of an analyte. Such processes are known to the expert in the field of immunoassays (see, for example, Annals of Clinical Chemistry, 16, 221/1979). These processes are altered in that the determination necessary therein of the hydrolase-labelled immunologically active compounds is carried out by means of the process according to the present invention. By way of example, there may be mentioned:

When the analyte is an antigen or hapten, the following processes have proved to be useful:

The sample solution containing the analyte is mixed with an excess of conjugate of an antibody against the analyte and of a hydrolase, an immune complex being formed of analyte and conjugate. The excess of conjugate is bound by immune reaction to a carrier to which is bound an excess of analyte or of an analyte-analogous compound. The solution containing the conjugate of hydrolase and immune complex is separated from the carrier and treated according to the process of the present invention. There is obtained an experimental result for the hydrolase conjugate from which can be deduced the presence or the amount of an analyte. Another possibility is the detection of the conjugate of hydrolase and antibody bound to the carrier. This is also possible by the process according to the present invention.

The sample solution containing the analyte is mixed with an excess of conjugate of an antibody against the analyte and of a hydrolase, an immune complex of analyte and conjugate being formed. The excess of conjugate is bound by immune reaction to a carrier to which is bound an excess of a further antibody against the analyte. The solution containing the excess of the conjugate of hydrolase and antibody is separated from the carrier and, according to the process of the present invention, there is determined either the conjugate of immune complex and hydrolase bound to the carrier or the conjugate of antibody and hydrolase contained in the solution.

The sample solution containing the analyte is mixed with a known amount of conjugate of analyte or analyte analogue and of a hydrolase. The mixture is applied to a carrier to which is bound a known insufficiency of an antibody against the analyte and the analyte analogue, referred to the sum of analyte and conjugate.

A part of the analyte and of the conjugate is bound to the carrier. According to the process of the present invention, after separation of the solution, there can be determined either the conjugate bound to the carrier or the conjugate present in the solution.

If the analyte is an antibody, the same principles can be used but, instead of the antibody, in the above-described process there must then be used an antigen or an antibody directed against the antibody.

In immunological processes for the detection of an analyte, the detection of the hydrolase conjugate according to the process of the present invention is followed by the evaluation. From the presence or, in the case of quantitative evaluation, the amount of the detected hydrolase conjugate can, namely, be deduced the presence or the amount, respectively, of the analyte in the sample originally used. This can take place, for example, by means of a calibration curve.

Furthermore, the process according to the present invention can be used for the detection of a substance with hydrolase activity in processes for the detection of nucleic acids. Such processes are known to experts in the field of nucleic acid hybridisation tests. In these tests, there are detected single-strand or double-strand nucleic acids, especially DNA or RNA or fragments thereof which are bound to a hydrolase as enzyme label, the amount of which is a measure for the concentration of the nucleic acid to be detected. The detection of these hydrolase-labelled nucleic acids takes place in an advantageous way according to the process of the present invention for the detection of a substance with hydrolase activity.

The advantages of this new immunological process and of the new process for the detection of nucleic acids is given from the advantages of the process according to the present invention for the detection of substances with hydrolase activity.

The present invention also provides an agent for the detection of substances with hydrolase activity which contains at least one compound of general formula (I). Such an agent can be used for the detection of substances with hydrolase activity in a sample to which an oxidation agent is added previously, simultaneously or subsequently.

An agent for the detection of substances with hydrolase activity is preferred which contains at least one compound of general formula (I) and an oxidation agent.

Furthermore, the agent can contain additives which are admittedly not necessary for the actual detection reaction but nevertheless exercise an advantageous action. These include especially buffer substances which permit the detection reaction to be carried out at a constant pH value. Also included are wetting agents, which bring about a uniform wetting of carrier materials, and detergents.

The agent according to the present invention preferably comprises one or more absorbent or swellable carriers. Such carriers are, for example, fleece or films, fleece being preferred. Sponge-like or porous carriers can also be used.

These agents preferably contain one or more absorbent or swellable carriers on which the hydrolase substrate and the oxidation agents are impregnated together or separately or, in the case of films, are incorporated therein. The production of such agents takes place according to known processes.

Apart from the hydrolase substrate and the oxidation agent, as well as additives possibly present, the agent according to the present invention can also contain a solvent, the preferred solvent being water. Here, too, the hydrolase substrate and the oxidation agent can be present as solution together or separately.

The agent according to the present invention can also be present in the form of one or more powders of powder mixtures. Apart from the hydrolase substrate and the oxidation agent, such an agent can preferably also contain preferably inert, soluble galenical filling materials, such as polyvinylpyrrolidone, polyethylene glycols and the like. The powders or powder mixtures can also be pressed into tablets.

Such an agent can be used in a process for the detection of substances with hydrolase activity.

For the detection of substances with $\beta$-galactosidase activity, compounds of the following general formula (IV), in which X' is a $\beta$-galactoside residue, are especially preferred, these compounds being new.

Therefore, the present invention also provides compounds of the general formula:

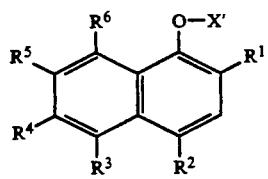

(IV)

wherein $R^1$, $R^2$, $R^3$, $R^4$, $R^5$ and $R^6$ have the above-given meanings and X' is a $\beta$-galactoside residue.

These compounds are characterised in that they can be advantageously used in the process according to the present invention for the detection of substances with $\beta$-galactosidase activity since they are $\beta$-galactosidase substrates.

The present invention also provides a process for the preparation of compounds of general formula (IV), wherein a compound of the general formula:

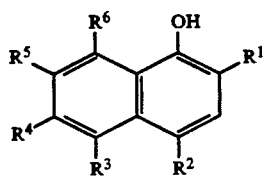

(II)

in which $R^1$ to $R^6$ have the above-given meanings, is reacted with a compound of the general formula:

$$X'-Y \qquad (V)$$

in which X' is a β-galactosyl residue and Y is a reactive group, possibly with the use of protective groups.

The present invention is also concerned with the use of compounds of general formula (I) wherein $R^1$, $R^2$, $R^3$, $R^4$, $R^5$, $R^6$ and X have the above given meanings in the above-described process for the detection of substances with hydrolase activity.

The following Examples are given for the purpose of illustrating the present invention:

EXAMPLE 1 a)
4-Methoxy-1-naphthyl-2,3,4,6-tetra-O-acetyl-β-D-galactopyranoside 96.1 g. (233.6 mMole) acetobromogalactose (1-bromo-2,3,4,6-tetra-O-acetyl-α-D-galactopyranose: Fluka) are dissolved in 200 ml. acetone and deoxygenated by passing in nitrogen. The solution is heated to the boil with continuous stirring and then there is added dropwise first a solution of 14.3 g. (254.9 mMole) potassium hydroxide in 13 ml. water and subsequently a solution of 18.5 g. (106.2 mMole) 4-methoxy-1-naphthol (Liebigs Ann. Chem., 140/1980) in 200 ml. acetone, in each case within the course of 10 minutes. During the addition, the reaction mixture should boil continuously under reflux. Subsequently, stirring is continued for 4 hours at the same temperature, then cooled, filtered off from insolubles and the filtrate evaporated in a high vacuum. The syrupy residue is digested three times with, in each case, 100 ml. water and then used as crude product, without further purification, in the next step of the synthesis. TLC (silica gel 60 (Merck), elution agent chloroform/ethyl acetate 20:1 v/v, $R_F=0.40$.

b) 4-Methoxy-1-naphthyl-β-D-galactopyranoside

To a suspension of the compound from Example 1a) in 150 ml. anhydrous methanol is added, with the exclusion of moisture, within the course of 1 hour. 25 ml. of a 0.5M sodium methanolate solution in anhydrous methanol so that the pH value of the reaction mixture is kept at about 13. After conclusion of the reaction (TLC monitoring), the product is isolated by column chromatography on silica gel. Yield 10 g. TLC (silica gel 60, elution agent chloroform/methanol 3:1 v/v), $R_F=0.40$.
$^1$H-NMR (DMSO-$d_6$): δ(ppm)=3.41-3.80 (m, 6H); 3.92 (s,3H); 4.52-4.89 (m, 4H); 5.31 (d, J=5 Hz, 1H); 6.84 (d, J=8.5 Hz, 1H); 7.16 (d, J=8.5 Hz, 1H); 7.47-7.60 (m, 2H); 8.08-8.17 (m, 1H); 8.31-8.41 (m, 1H).

MS (pos. FAB): m/e=337.

EXAMPLE 2

4-Chloro-1-naphthyl-β-D-galactopyranoside

From 4-chloro-1-naphthol (Aldrich) and acetobromogalactose there is prepared, analogously to the procedure of Example 1a) and 1b), 4-chloro-1-naphthyl-β-D-galactopyranoside. TLC (silica gel 60, elution agent chloroform/methanol 7:3 v/v), $R_F=0.57$ $^1$H-NMR (DMSO-$d_6$): δ(ppm)=3.30-3.95 (m, 10H); 5.05 (d, J=5 Hz, 1H); 7.24 (d, J=8.5 Hz, 1H); 7.61-7.85 (m, 3H); 8.13-8.22 (m, 1H); 8.40-8.53 (m, 1H).

EXAMPLE 3

4-Propoxy-1-naphthyl-β-D-galactopyranoside

From 4-propoxy-1-naphthol (Liebigs Ann. Chem., 140/1980) and acetobromogalactose is prepared, analogously to the procedure according to Example 1a) and 1b), 4-propoxy-1-naphthyl-β-D-galactopyranoside. TLC (silica gel 60, elution agent chloroform/methanol 3:1 v/v), $R_F=0.42$.

$^{13}$C-NMR (CD$_3$OD): δ(ppm)=11.09, 23.78, 62.44, 70.30, 71.02, 72.55, 75.07, 76.94, 104.28, 105.39, 111.52, 122.65, 123.27, 128.45, 126.80, 127.61, 128.43, 148.51, 151.57.

MS ((TMS)$_4$ derivative): m/e =652.

EXAMPLE 4

4-Isopropoxy-1-naphthyl-β-D-galactopyranoside

From 4-isopropoxy-1-naphthol and acetobromogalactose is prepared, analogously to the procedure of Example 1a) and 1b), 4-isopropoxy-1-naphthyl-β-D-galactopyranoside. TLC (silica gel 60, elution agent chloroform/methanol 3:1 v/v), $R_F=0.53$.

MS (neg. FAB): m/e=363.

EXAMPLE 5

4-Benzyloxy-1-naphthyl-β-D-galactopyranoside

From 4-benzyloxy-1-naphthol (Liebigs Ann. Chem., 140/1980) and acetobromogalactose is prepared, analogously to the procedure of Example 1a) and 1b), 4-benzyloxy-1-naphthyl-β-D-galactopyranoside. TLC (silica gel 60, elution agent chloroform/methanol 3:1 v/v), $R_F=0.46$.

MS ((TMS)$_4$ derivative): m/e=700.

EXAMPLE 6

4-Trifluoroethoxy-1-naphthyl-β-D-galactopyranoside

From 4-trifluoroethoxy-1-naphthol (Z. Naturforsch., 40b, 534/1985) and acetobromogalactose is prepared, analogously to the procedure of Example 1a) and 1b), 4-trifluoroethoxy-1-naphthyl-β-D-galactopyranoside. TLC (silica gel 60, elution agent chloroform/methanol 3:1 v/v), $R_F=0.42$.

$^H$-NMR (CD$_3$OD): δ(ppm) =3.46-3.93 (m, 6H); 4.57 (q, J=9 Hz, 2H); 4.86 (d, J=6 Hz, 1H); 6.81 (d, J=8 Hz, 1H); 7.09 (d, J=8 Hz, 1H); 7.38-7.48 (m, 2H); 7.99-8.09 (m, 1H), 8.25-8.35 (m, 1H).

EXAMPLE 7

2-Methoxy-1-naphthyl dihydrogen phosphate

In a 500 ml. three-necked flask equipped with a stirrer, thermometer and dropping funnel is placed a solution of 13.07 g. (0.075 mole) 2-methoxy-1-naphthol (J. Chem. Soc., 2316/1967) in 150 ml. pyridine and, while cooling to 0°-5° C., 11.5 g. (6.9 ml., 0.075 mole) phosphorus oxychloride are added dropwise thereto, while stirring. After 2 hours, the residue is filtered off with suction and the filtrate is poured on to 200 g. ice. After 5 minutes stirring, the pH value is adjusted to 8 with a concentrated aqueous solution of sodium hydroxide and the yellow solution is evaporated in a vacuum. The pale residue is stirred with acetone and filtered off with suction. The crude product obtained is dissolved in 200 ml. hot water, insoluble components are filtered off with suction, the mother liquor is mixed with concentrated hydrochloric acid until the phosphoric acid ester precipitates out, this is filtered off with suction and the reaction product is dried to constant weight in a vacuum over phosphorus pentoxide. There are obtained 16 g. of colourless crystals of 2-methoxy-1-naphthyl dihydrogen phosphate; m.p. 171° C., MS: m/e=254.18. TLC (silica gel 60 Merck, elution agent isopropanol/-butyl acetate/water 50:30:20 v/v/v), $R_F$=0.38.

$^1$H-NMR (D$_2$O, NaOD): δ(ppm)=3.98 (s, 3H); 7.42 (ddd, J=8.2, 6.8 and 1.3 Hz, 1H); 7.46 (d, J=8.8 Hz, 1H); 7.55 (ddd, J=8.2, 6.8 and 1.3 Hz, 1H); 7.71 (d, J=9.0 Hz, 1H); 7.86 (d, J=8.2 Hz, 1H); 8.36 (d, J=8.6 Hz, 1H).

EXAMPLE 8

4-Methoxy-1-naphthyl phosphate disodium salt 14.72 g. (0.1 mole) 4-methoxy-1-naphthol are dissolved in 200 ml. pyridine and 15.35 g. (9.16 ml., 0.1 mole) phosphorus oxychloride are added dropwise thereto with stirring and cooling with an ice-salt bath at 3° C. After stirring for 2 hours, the crystalline residue formed is filtered off with suction and the orange coloured filtrate dropped into 400 ml. ice water. With the help of a glass electrode and of a pH meter, the pH is adjusted to 8 by the dropwise addition of a concentrated aqueous solution of sodium hydroxide and the reaction mixture then evaporated to dryness at 50° C. on a rotary evaporator. There are obtained 18 g. of brown resin which is dissolved in 100 ml. hot isopropanol and the product then precipitated out by the addition of 300 ml. diethyl ether. There are obtained 16.8 g. 4-methoxy-1-naphthyl phosphate disodium salt.

$^1$H-NMR (D$_2$O, NaOD): δ(ppm)=4.02 (s, 3H), 6.98 (d, J=8.5 Hz, 1H); 7.38 (dd, J=8.5 and 1.5 Hz, 1H); 7.61, 8.19 and 8.31 (ABYZ system, 2 and each 1H).

EXAMPLE 9

1-Acetoxy-4-methoxynaphthalene 1.75 g. (10 mMole) 4-Methoxy-1-naphthol is boiled under reflux for 2.5 hours in 18 ml. acetic anhydride. Thereafter, the solution is evaporated in a vacuum and the oily residue purified by column chromatography (silica gel; toluene/ethyl acetate 40:1 v/v). After evaporation of the appropriate fractions, the crude product is recrystallised from petroleum ether (b.p. 90°–110° C.). Yield 1.27 g. (58% of theory) of colourless crystals; m.p. 51°–53° C.

EXAMPLE 10

Detection of human chorionic gonadotropin (hCG) in a sample

A) Preparation of a Test Carrier (FIG. 1)

a) Preparation of Fleece 3

A piece of paper (Type 4210 of the firm Kalff) was cut up into a strip (2.6 cm. long and 0.6 cm. wide). 20 μl. of a solution of 40 mg./ml. 4-methoxy-1-naphthyl-β-D-galactopyranoside (galactosidase substrate) in dimethyl sulphoxide were mixed with 20 μl. of a 24% solution of polyvinyl alcohol in water. This mixture was applied to the middle of the paper strip.

b) Preparation of Fleece 5

A piece of paper (Type 4210 of the firm Kalff) was cut up into a strip (2.6 cm. long and 0.6 cm. wide). One end was impregnated with 100 μl. PBS buffer (phosphate buffered saline, pH 7.0, 1% bovine serum albumin, 0.1% Tween ® 20). To the middle of the strip was applied 7.5 μl. of a solution which contained 20 U/ml. of a conjugate of a Fab fragment of a monoclonal antibody against hCG and β-galactosidase (substance with galactosidase activity), 100 μg./ml. of a monoclonal mouse antibody against the μ-chain of hCG and 7.5 mg./ml. 4-aminobenzyl-1-thio-β-D-galactopyranoside. The end which lies opposite the buffer-impregnated end was impregnated with 10 μl. of a 5% solution of polyvinyl alcohol in water.

c) Preparation of Fleece 6

On to a piece of paper (Type 3512 of the firm Schleicher & Schull) was fixed, after activation with cyanogen bromide, sheep antibody against the Fc part of mouse antibodies. A piece of this material was cut up into a strip (length 1.1 cm., width 0.6 cm.).

d) Preparation of Fleece 7

A piece of paper (Type D-28 of the firm Whatman) was cut up to the size of 5×0.6 cm.

e) Fleece 3 and 5 were separated from one another by a plastic film 4.

By sticking the dried fleece on to a base film 2 with a breadth of 0.6 cm., there was produced the test carrier 1 illustrated in FIG. 1 of the accompanying drawings. Fleece 5 was thereby stuck on in such a manner that the end impregnated with polyvinyl alcohol showed in the direction of the end 8 of the test carrier.

B) Carrying Out of the Test a) Sample Preparation 0.5 ml. of sample was mixed with 0.5 ml. of a solution which contained 4 mMole/l. sodium perborate and 10 mg./l. horseradish peroxidase (oxidation agent) in phosphate buffer (pH 7).

b) Application of the Sample to the Test Strip

The end 8 of the test strip 1 was placed in the solution. The hCG-containing solution penetrated into the fleece 5 and fleece 3 and dissolved the substances present thereon. By reaction of hCG with the β-galactosidase-labelled Fab fragment of a monoclonal antibody against hCG and the monoclonal antibody against the β chain of hCG, in the solution in fleece 5 was formed a β-galactosidase-labelled immune complex of the three components. This immune complex, which in this case represents the substance with hydrolase activity, was now detected by means of the process according to the present invention in fleece 6. The solution with the immune complex penetrated just like the solution with the substrate from fleece 3 into fleece 6 and was there mixed with this substrate solution. In fleece 6 the immune complex formed, as well as the excess of the monoclonal antibody against the β chain, was bound to fleece 6 via the fixed sheep antibody. A possible excess of β-galactosidase-labelled Fab fragment flowed further into fleece 7. Due to the β-galactosidase labelling of the bound immune complex and with the help of the oxidation agent, a blue colour was formed in fleece 6 within the course of 10 minutes.

If no hCG was present in the sample, then no β-galactosidase-labelled immune complex could be formed. Therefore, no substance with hydrolase activity is bound in fleece 6 and thus no colour development takes place. On the other hand, the total amount of β-galactosidase-labelled Fab fragment is still contained in the solution, which penetrates into the fleece 7. Therefore, a colour development is found in fleece 7 which comes from the reaction of the β-galactosidase-labelled Fab fragment which is also a substance with hydrolase activity. Thus a control of the test thereby takes place in that the process according to the present invention is also carried out in fleece 7. This is especially important when no hCG was present in the sample.

The evaluation can also take place quantitatively since the more hCG is present in the sample and thus bound β-galactosidase-labelled immune complex is present in fleece 6 the more intensive is the coloration in fleece 6 after a period of 10 minutes.

EXAMPLE 11

Detection of Thyroxin (T4)

Figure 2:
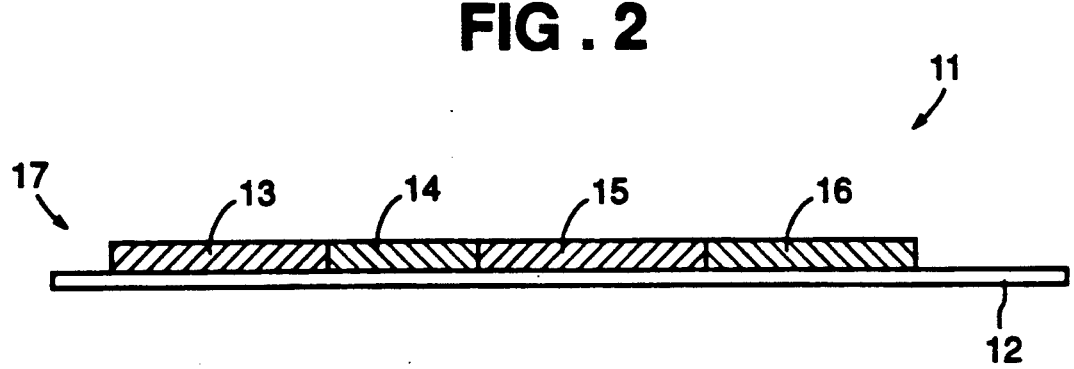

A) Preparation of a Test Strip 11 (FIG. 2)

a) Fleece 14

Fleece 14 is impregnated with a conjugate of β-galactosidase with an antibody against T4.

b) Fleece 15

A piece of paper (Schleicher & Schull 3512) was activated with cyanogen bromide and T4 succinimide ester bound thereon.

c) Fleece 16

Fleece 16 is a fleece which has been impregnated with 4-methoxy-1-naphthyl-β-D-galactopyranoside.

d) Fleece 13 serves for the application of sample.

For the production of the carrier 11 the fleeces are fixed on to a base film 12 as shown in FIG. 2.

B) Carrying Out of the Test a) Sample Preparation

The sample was prepared analogously to Example 10.

b) Carrying Out

The test strip was placed with the end 17 in the solution. The T4-containing sample penetrated into fleece 13. From there, it flowed further into fleece 14 from which it dissolved off the β-galactosidase conjugate. By immune reaction of the antibody with T4, there was formed a β-galactosidase-labelled immune complex. The solution which now contained, besides the immune complex, also an excess of the β-galactosidase conjugate, penetrated into fleece 15. This excess was there bound on to the paper via bound T4.

The solution which still contained the immune complex penetrated into fleece 16. The process according to the present invention for the detection of the β-galactosidase-labelled immune complex, which represents the substance with hydrolase activity, there takes place. The more of this complex and thus also of T4 was present in the solution, the more strongly was fleece 16 blue coloured after 10 minutes. In the case of the absence of T4, fleece 16 remained white. Various embodiments of the devices and methods described and claimed herein will of course be evident to the skilled artisan. The examples given herein are in no way to be construed as limitative of the broad disclosure.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

What is claimed is:

1. In a process for the detection of hydrolase activity by mixing a hydrolase-containing sample with a hydrolase substrate and an oxidizing agent and then evaluating the resultant colour intensity, the improvement which comprises employing as the hydrolase substrate a compound of the formula

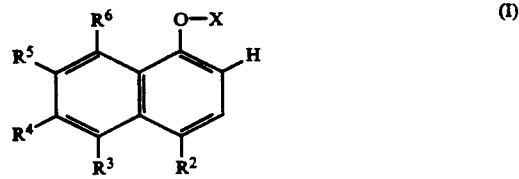

in which
R² is C₁–C₄ alkoxy;
  each of R³, R⁴, R⁵ and R⁶, which can be the same or different, is hydrogen; halogen; carboxy; carbamoyl optionally substituted once or twice by acetyl or C₁–C₄ alkyl; sulpho; amino optionally substituted once or twice by acetyl or C₁–C₄ alkyl; C₁–C₄ alkyl; C₁–C₄ alkoxy optionally substituted by halogen or amino; the group

in which n is a whole number from 1 to 3 and R⁷ is hydrogen, C₁–C₄ alkyl or a radical of formula (I) without the hydrogen atom; aralkoxy having from 6 to 10 carbon atoms in the aryl moiety and from 1 to 4 carbon atoms in the alkyl moiety; C₁–C₄ alkylcarbonyl; or C₁–C₄ alkoxycarbonyl; and
X is a glycosyl residue, a phosphate residue, an acyl residue having from 2 to 20 carbon atoms or an aminoacyl residue of a naturally occurring α-L-amino acid;
or R³ and R⁴ and/or R⁵ and R⁶ together form a benzene ring; and using no further coupling components.

2. The process according to claim 1 in which, in the compound,
X is a mono-, oligo- or poly-saccharide of the hexosepyranoside series; a saturated or unsaturated, straight-chain or branched-chain acyl or aminoacyl radical containing up to 20 carbon atoms; or the —PO₃H₂ radical and its alkali metal, alkaline earth metal and ammonium salts.

3. The process according to claim 2, in which X is a monosaccharide of a glucoside or a galactoside radical; acetyl; a residue of a naturally-occurring α-L-amino acid bound via the carbonyl function; or the —PO₃H₂ radical or its sodium, potassium, magnesium or calcium salts.

4. The process according to claim 3, in which X is a β-galactosyl.

5. The process according to claims 2, 3 or 4 in which R² is methoxy, isopropyoxy, n-propoxy or n-butoxy; each of R³, R⁴, R⁵ and R⁶, which can be the same or different, is hydrogen, chlorine, carboxy, unsubstituted carbamoyl, unsubstituted amino, methoxy, isopropoxy, n-propoxy, n-butoxy, 1,1,1-trifluoroeth-2-oxy, 1-bromoeth-2-oxy,

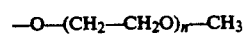

in which n is a whole number from 1 to 3, benzyloxy, methylcarbonyl or methoxycarbonyl.

6. The process according to claim 4 in which the hydrolase substrate is 4-methoxy-1-naphthyl-$\beta$-D-galactopyranoside.

7. A process according to claim 1, which takes place on an absorbent or swellable carrier.

8. A process according to claim 7, in which the evaluation is done visually.

9. The process according to claim 5 in which $R^2$ is methoxy, isopropoxy or n-propoxy, and $R^3$ $R^4$, $R^5$ and $R^6$ are hydrogen.

* * * * *

UNITED STATES PATENT AND TRADEMARK OFFICE
CERTIFICATE OF CORRECTION

PATENT NO. : 5,202,233
DATED : April 13, 1993
INVENTOR(S) : Rupert Herrmann, et al.

It is certified that error appears in the above-indentified patent and that said Letters Patent is hereby corrected as shown below:

Col. 6, line 45: delete "36" and insert -- $\underline{36}$ --.

Col. 6, line 60: delete "ah" and insert -- an --.

Col. 8, line 14: delete "16" and insert -- $\underline{16}$ --.

Col. 16, line 4: delete "µ" and insert -- β --.

Signed and Sealed this

Sixth Day of September, 1994

Attest:

BRUCE LEHMAN

Attesting Officer — Commissioner of Patents and Trademarks